United States Patent [19]
Kidwell

[11] 3,954,884
[45] May 4, 1976

[54] METHOD FOR PRODUCING BETA HYDROXY ETHYLENE GLYCOL ETHERS

[75] Inventor: Roger L. Kidwell, Kirkwood, Mo.

[73] Assignee: Monsanto Company, St. Louis, Mo.

[22] Filed: July 24, 1972

[21] Appl. No.: 274,713

Related U.S. Application Data

[63] Continuation-in-part of Ser. No. 2,350, Jan. 12, 1970, abandoned.

[52] U.S. Cl. .................. 260/615 R; 260/615 B
[51] Int. Cl.² .............. C07C 41/02; C07C 41/10
[58] Field of Search .............. 260/615 B, 615 R

[56] References Cited
UNITED STATES PATENTS

| | | | |
|---|---|---|---|
| 2,293,868 | 8/1942 | Toussaint | 260/615 B X |
| 2,327,053 | 8/1943 | Marple et al. | 260/615 B X |
| 2,380,185 | 7/1945 | Marple et al. | 260/615 B |
| 2,510,540 | 6/1950 | Ballard et al. | 260/615 B |
| 2,723,294 | 11/1955 | Benoit | 260/615 B |
| 3,081,354 | 3/1963 | Gaertner et al. | 260/615 B X |
| 3,188,353 | 6/1965 | Holtschmidt | 260/615 B |
| 3,240,819 | 3/1966 | Gaertner et al. | 260/615 R |
| 3,242,200 | 3/1966 | Johnson | 260/398 |
| 3,427,248 | 2/1969 | Lamberti et al. | 260/615 B X |
| 3,607,778 | 9/1971 | Lincoln et al. | 260/615 B UX |

*Primary Examiner*—Howard T. Mars
*Attorney, Agent, or Firm*—N. E. Willis; J. E. Maurer; T. N. Wallin

[57] ABSTRACT

This invention relates to methods for rapidly producing beta hydroxy ethylene glycol ethers by reacting internal epoxyalkanes with mono or poly ethylene glycols in the presence of critical amounts of acidic catalysts under controlled temperature conditions.

4 Claims, No Drawings

METHOD FOR PRODUCING BETA HYDROXY ETHYLENE GLYCOL ETHERS

BACKGROUND OF THE INVENTION

This invention is a continuation-in-part of U.S. patent application Ser. No. 2,350, filed Jan. 12, 1970 and now abandoned and relates to a process for producing beta hydroxy glycol ethers.

More particularly, the invention relates to a process of preparing such compounds by reaction of internal epoxyalkanes with mono or poly ethylene glycols in the presence of acidic catalysts.

Beta hydroxy glycol ethers are effective detergent surfactants. Structurally, these compounds are linear alkane chains internally vicinally substituted with hydroxy and ethylene glycol groups. These compounds are represented by the formula

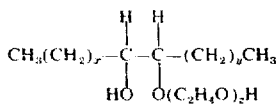

wherein $x$ and $y$ are integers from 0 to 16, the sum of $x$ and $y$ being from 8 to 16 and $z$ is an integer from 1 to 5.

In certain detergent applications, such compounds are believed to provide advantages as compared to isomers thereof wherein the hydroxy and glycol substituents occupy terminal positions on the alkane chain. Belgian Pat. No. 729,285 (corresponding to U.S. Pat. application, Ser. No. 710,644, filed Mar. 5, 1968, now abandoned) provides a detailed disclosure of the surfactant properties and applications of the compounds produced by the process of this invention.

It is well known that alkanes terminally vicinally substituted with hydroxy and ether substituents, can be prepared by reaction of a terminal epoxyalkane with a glycol in the presence of a catalyst. Such reactions are described in U.S. Pat. Nos. 3,242,200, 2,327,053, and 3,240,819. However, when internal epoxyalkanes are substituted for terminal epoxyalkanes in such processes, difficulties are encountered which render it apparent that the generalized processes described for production of the terminal isomers are not suitable for commercial production of the internal isomers. For example, the generalized teachings of the prior art indicate the suitability of alkaline catalysts for the reactions described. However, when alkaline catalysts are utilized with internal epoxyalkane reactants in reactions of the type described, little or no reaction takes place. When acidic catalysts are utilized under reaction conditions suggested as being preferred (temperatures below 100°C) it is found that major proportions of the epoxyalkanes are rearranged to ketones and high boiling impurities and that correspondingly low yields of the desired product are obtained. Although it might be expected that the formation of undesired products could be minimized by use of lower temperatures and lower levels of catalysts, such modifications of previously described processes were not found to provide significant improvements.

The need for a method of preparing the internal isomers in high yields with minimum by-product formation was, therefore, prior to the present invention, apparent to those familiar with the art.

SUMMARY OF THE INVENTION

It is an object of this invention to provide processes for production of beta hydroxy ethylene glycol ethers in high yields with minimum formation of by-products.

Basically, these objects are accomplished by reacting internal epoxyalkanes with mono or poly ethylene glycols in the presence of critical amounts of specific acidic catalysts under controlled temperature conditions substantially higher than those generally preferred for production of terminal isomers. The process and the advantages provided thereby will be understood from the following description of the preferred embodiments.

DESCRIPTION OF THE PREFERRED EMBODIMENTS

The reactants utilized in the process of this invention are internal epoxyalkanes and mono and poly ethylene glycols.

The internal epoxyalkanes are represented by the formula:

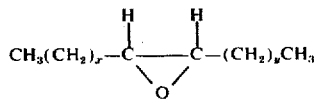

wherein $x$ and $y$ are integers from 0 to 16, the sum of $x$ and $y$ being from 8 to 16.

Such compounds can be prepared by procedures such as described in Kirk-Othmer, *Encyclopedia of Chemical Technology*, Second Edition, Volume 8, p. 238 (1965). A preferred method of preparation of such compounds is the epoxidation of internal olefins (obtained, for example, by catalytic dehydrogenation of linear paraffins or by isomerization of alpha olefins) by epoxidation procedures such as described by Swern, Billen and Scanalan, *Journal Of The American Chemical Society*, 68, p. 1507–1508 (1946). Methods of preparing the epoxides are also described in Belgian Pat. No. 729,285.

From the standpoint of performance of the final surfactant product it is preferred that a mixture of various internal isomeric forms of the epoxyalkanes be utilized in the reaction, for example, a mixture of 2,3; 3,4, etc. position isomers. From the viewpoint of raw material economy, a mixture of homologs of the epoxyalkanes is also preferred, an average alkyl chain length of 16 carbon atoms (the sum of x and y is 12) being preferred for optimum surfactant performance. Either the cis or trans forms of the epoxyalkanes or mixtures thereof may be utilized in the practice of this invention.

The glycols utilized as reactants in the practice of this invention are represented by the formula:

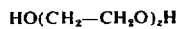

wherein $z$ is an integer from 1 to 5 inclusive. The invention can be practiced using commercially available glycols identified as having average molecular weights commensurate with a value of $z$ from 1 to 5. Such commercial glycols will normally contain minor amounts of glycols outside this range but this does not adversely effect the practice of this invention. The use of monoethylene glycol ($z$ equals 1) is preferred.

In the practice of this invention, the glycol and epoxide reactants should be admixed in a glycol to epoxide mole ratio of at least 6:1, preferably 8:1. Higher ratios can be utilized without adverse effect but ratios greater than 10:1 generally do not provide any significant additional advantages with respect to reaction rate and product purity. When the process of the invention is operated continuously, higher ratios, for example, 20:1 to 50:1, may, in some instances, provide a convenient heat transfer medium to facilitate temperature control.

In the process of this invention, the reaction of the glycol and epoxyalkane is catalyzed by an acidic catalyst represented by the formula:

wherein R is —OH, alkyl, alkyl—O—, or aryl. For example, the reaction may be catalyzed by sulfuric acid; alkyl sulfonic acids, such as ethane, butane, hexane, or decane sulfonic acids; aryl sulfonic acids such as benzene sulfonic acid, toluene sulfonic acid, xylene sulfonic acid, naphthalene sulfonic acid, sulfonated polystryene, or sulfonated styrene-divinyl benzene copolymers; and sulfuric acid mono alkyl esters, e.g. ethyl sulfuric acid. The use of sulfuric acid as a catalyst is particularly preferred.

The use of sulfonic or sulfuric acid catalysts as discussed above is essential to the successful practice of the present invention. The advantages of the invention are not obtained with other conventional catalysts such as acetic acid, phosphoric acid and the like.

In addition, in order to obtain the advantages of the present invention, it is essential to use critical amounts of catalyst as hereinafter specified. Specifically, the advantages of the present invention are obtained by the utilization of from 0.0025 equivalents to 0.015 equivalents of acid catalyst per mole of epoxyalkane. The use of lesser amounts does not effectively catalyze the reaction whereas the use of greater amounts results in formation of undesirably high amounts of by-products and/or product discoloration.

In the process of this invention, the reaction is conducted under continuous agitation in order to maintain an intimate mixture of the two phases present in the reaction medium.

The reaction is initiated at a temperature of at least 135°C and, during the course of the reaction, raised to at least 150°C but not above 180°C. Preferably, the reaction is initiated at about 150°C and raised to a temperature of at least 165°C but not greater than 170°C. This can be conveniently and economically accomplished merely by mixing the reactants and catalyst at an initial temperature of from 135°C to 150°C and permitting the exothermic nature of the reaction to raise the temperature to the levels indicated above.

The temperature conditions of the reaction as set forth above are highly critical in that if higher temperatures are utilized, product decomposition occurs whereas if lower temperatures are utilized, rearrangement of the epoxyalkanes to ketones and formation of high boiling impurities significantly reduces product yields.

The pressure under which the reaction is conducted can be varied within a wide range as long as the pressure is not so low as to result in excessive vaporization of raw material or catalyst. The reaction can be successfully conducted over a pressure range of from about 0.5 to 10 atmospheres with a pressure range of from 1 to 4 atmospheres being preferred.

The catalyst should not be added to the epoxide or combined reactants below the initial temperature specified in order to avoid side reactions.

The product can be separated by conventional techniques. For example, when monoethylene glycol is utilized, the reaction medium can be cooled to 40°C or lower, resulting in separation of the mixture into two liquid phases. The top phase contains the product and some glycol which can be removed by distillation. When polyethylene glycols are utilized, addition of water effects separation of the mixture into two phases.

The practice of the invention is further illustrated by the following examples:

EXAMPLE I

Into a conventional mixing vessel equipped with a stirrer and condenser are charged 30.06 g. (0.125 mole) of a mixture of epoxyalkanes wherein the compounds making up the mixtures fall within the following formula:

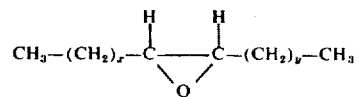

and $x$ and $y$ are numbers from 0 to 14 and the sum of $x$ and $y$ is from 9 to 14 with the average chain length of the compounds making up the mixture being about 16 (hereinafter referred to as an average $C_{16}$ epoxyalkane) and 62.07 g. (1.0 moles) of monoethylene glycol and heated to a temperature of 150°C. 0.06 g. of 98% by weight $H_2SO_4$ is added and after 20 seconds the temperature has risen to 168°C and then decreases to 150°C, after about 3 minutes. The reaction mixture is then cooled to about 40°C and the two phases are separated. Vapor phase chromatography analysis is used to determine the product, the high boilers and low boiler (i.e., ketones, unreacted epoxyalkanes and ketals boiling below that of the product).

The above procedure was followed in obtaining the product set forth in Table 1, Run 1. In addition, the same procedure was utilized in Runs 2 - 5.

TABLE 1

| Run | Average $C_{16}$ Epoxyalkane g | mole | Ethylene glycol g | mole | Moles glycol Moles epoxyalkane | $H_2SO_4$ (% of epoxyalkane) | Temp. °C Initial | Max. | Reaction time | % L.B.[2] | % H.B.[3] | % Product |
|---|---|---|---|---|---|---|---|---|---|---|---|---|
| 1 | 30.1 | 0.125 | 62.1 | 1.0 | 8:1 | 0.06 | 150 | 168 | 20 sec. | 1.9 | 1.3 | 96.8 |
| 2 | 30.1 | 0.125 | 62.1 | 1.0 | 8:1 | 0.06 | 80 | | No Reaction | — | — | — |
| 3 | 30.1 | 0.125 | 62.1 | 1.0 | 8:1 | none | 175 | 190 | No Reaction | — | — | — |
| 4 | 30.1 | 0.125 | 62.1 | 1.0 | 8:1 | 3.3[1] | 150 | | No Reaction | — | — | — |

TABLE 1-continued

| Run | Average C_{16} Epoxyalkane g | mole | Ethylene glycol g | mole | Moles glycol Moles epoxyalkane | $H_2SO_4$ (% of epoxyalkane) | Temp. °C Initial | Max. | Reaction time | % L.B.[2] | % H.B.[3] | % Product |
|---|---|---|---|---|---|---|---|---|---|---|---|---|
| 5 | 30.1 | 0.125 | 62.1 | 1.0 | 8:1 | 0.18 | 150 | 170 | 20 sec. | 6.8 | 3.4 | 89.9 |

[1]acetic acid
[2]low boiler
[3]high boiler

As can be seen from Table 1, Run 1, by utilizing the process of this invention, high yields of the product are obtained with correspondingly low yields of low boilers and high boilers. Likewise, as demonstrated by Run 2, the temperature is not within the range set forth in the specification, and consequently, there is no reaction. Additionally, if no catalyst is employed, there is no reaction. Run 4 demonstrates that the use of a catalyst other than those specified does not yield the advantages of the present invention. Run 5 demonstrates that when the catalyst employed in the process of this invention in an amount outside the preferred range, the percent of the product recovered is decreased. Additionally, a visual inspection indicated that poor color was obtained.

Equally good results are obtained when 0.125 mole of a mixture of epoxyalkanes wherein the compounds making up the mixture have the formula

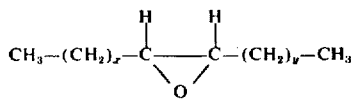

where $x$ and $y$ are from 0 to 11, the sum of $x$ and $y$ is from 12 to 15 and the average chain length of the compounds is about 13 is substituted for 0.125 mole of average $C_{16}$ epoxyalkane used in Example I.

Satisfactory results are obtained by substituting one mole of diethylene glycol for monoethylene glycol.

EXAMPLE II

The procedure of Example I was repeated except the amount of epoxyalkane was varied as listed in runs 1 – 8 in Table 2, the amount of catalyst was varied, and the initial temperature varied. The results are shown in Table 2 below.

tions of this invention, as exemplified by Run 8, are apparent.

EXAMPLE III

To illustrate a continuous process, a reactor which consists of a 250 ml. 3 neck flask fed by two sections of ¼ inch stainless steel tubing that are wrapped with heating elements is utilized. The temperature of the epoxyalkane (the same as used in Example I), monoethylene glycol and 98% sulfuric acid feed streams is adjusted by the voltage on these lines. Further heat and more precise temperature control for the glycol and acids stream is accomplished by the use of an oil bath. The epoxyalkane is fed to the reaction flask by a pump at the rate of 10 ml/min. In another container the ethylene glycol is charged along with 98% sulfuric acid, 0.075% by volume based on the weight of the glycol, and pumped at the rate of 70 ml/min. to the reaction flask. The glycol/acid mixture is maintained at a temperature of about 120°–140°C. Heat for the reaction flask is supplied at a high setting so that the temperature is maintained at about 165°C. The hot reactants then pass into a 12 inch section of a vacuum jacketed Vigreaux column which agitates the falling liquids and maintains reaction temperatures long enough for a complete conversion of epoxide to product. Then the two phases, product and ethylene glycol, are quickly cooled through a jacketed spiral water cooled condenser and then separated. The less dense product is easily decantated off of the glycol acid mixture at this point. The product yield is about 89% to about 91% with 4 – 5% high boiler and 5 – 6% low boiler.

The above procedure was followed running the process for 10 minutes yielding 100 gm of a 91% pure product and 4% of high boiler and 5% of low boiler.

What is claimed is:

1. A method of making a beta hydroxy ethylene gly-

TABLE II

| Run | Average C_{16} Epoxyalkane g | mole | Ethylene glycol g | mole | Moles glycol Moles Epoxyalkane | $H_2SO_4$ (% of epoxyalkane) | Temp. °C Initial | Max. | Reaction time | % L. B | % H. B | % Product |
|---|---|---|---|---|---|---|---|---|---|---|---|---|
| 1 | 218 | .91 | 62.1 | 1.0 | 1.1:1 | 0.5 | 100 |  | 30 min. | na | 47.9 | 52.1 |
| 2 | 120.2 | 0.5 | 62.1 | 1.0 | 2:1 | 0.5 | 100 | 110 | 30 min. | 5.6 | 20.3 | 74.1 |
| 3 | 120.2 | 0.5 | 62.1 | 1.0 | 2:1 | 0.5 | 100 | 130 | 30 min. | 10.0 | 20.0 | 70.0 |
| 4 | 120.2 | 0.5 | 62.1 | 1.0 | 2:1 | 5.0[1] | 100 |  | 120 min. | 17 | 30 | 53 |
| 5 | 79.5 | .33 | 62.1 | 1.0 | 3:1 | 0.65 | 100 | 118 | 40 min. | 2.5 | 17.1 | 80.5 |
| 6 | 60.0 | .25 | 62.1 | 1.0 | 4:1 | 1.2 | 125 | 145 | 4 min. | 6.3 | 9.6 | 84.1 |
| 7 | 60.0 | .25 | 62.1 | 1.0 | 4:1 | .2 | 125 | 145 | 4 min. | 2.5 | 7.4 | 90.1 |
| 8 | 41.0 | .17 | 62.1 | 1.0 | 6:1 | 0.15 | 135 | 150 | 90 sec. | 0.9 | 4.3 | 94.8 |

[1]anhydrous hydrogen fluiride

As can be seen from Table 2, Runs 1 – 4, when the optimum temperature range is not employed, the reaction times are longer and the yields are not as high. Runs 6 – 8 point out the effect of different mole ratios of glycol to epoxyalkane. It can be seen that, however, as the ratio increases, the product purity increases. The advantages of conducting the process within the limitacol represented by the formula

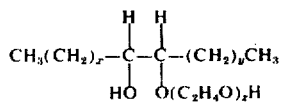

wherein x and y are integers from 0 to 16, the sum of x and y being from 8 to 16 and z is an integer from 1 to 5, said process comprising reacting an epoxyalkane represented by the formula

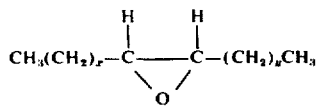

wherein x and y are whole numbers from 0 to 16, the sum of x and y being from 8 to 16 with a glycol represented by the formula

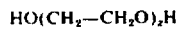

wherein z is an integer from 1 to 5 in the presence of an acidic catalyst represented by the formula

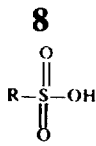

wherein R is selected from the group consisting of —OH, alkyl, alkyl—O—, and aryl, the molar ratio of glycol to epoxyalkane being at least 6:1, said catalyst being present in an amount of from 0.0025 equivalents to 0.015 equivalents per mole of epoxyalkane, the reaction being initiated at a temperature of at least 135°C and raised to a temperature of at least 150°C but not greater than 180°C.

2. The process of claim 1 wherein the molar ratio of glycol to epoxyalkane is at least 8:1.

3. The process of claim 1 wherein the reaction is initiated at a temperature of about 150°C and raised to a temperature of at least 165°C but not greater than 170°C.

4. The process of claim 3 wherein the molar ratio of glycol to epoxyalkane is at least 8:1.

* * * * *